United States Patent [19]
Riedel

[11] Patent Number: 5,801,817
[45] Date of Patent: Sep. 1, 1998

[54] METHOD AND APPARATUS FOR ELIMINATING THE EFFECTS OF VARYING SAMPLE DISTANCE ON OPTICAL MEASUREMENTS

[75] Inventor: Richard A. Riedel, Carmel, Ind.

[73] Assignee: UMM Electronics Inc., Indianapolis, Ind.

[21] Appl. No.: 851,415

[22] Filed: May 5, 1997

[51] Int. Cl.[6] .................................................. G01C 3/08
[52] U.S. Cl. .................................. 356/4.07; 356/445
[58] Field of Search ...................... 356/4.07, 39, 445

[56] References Cited

U.S. PATENT DOCUMENTS

| | | | |
|---|---|---|---|
| 3,788,741 | 1/1974 | Buechler | 356/4 |
| 3,815,994 | 6/1974 | Peckham | 356/4 |
| 4,639,140 | 1/1987 | Lerat | 356/376 |
| 4,647,193 | 3/1987 | Rosenfeld | 356/4 |
| 4,716,430 | 12/1987 | Stauffer | 354/403 |
| 5,028,139 | 7/1991 | Kramer et al. | 356/446 |
| 5,049,487 | 9/1991 | Phillips et al. | 435/4 |
| 5,159,412 | 10/1992 | Willenborg et al. | 356/445 |
| 5,699,164 | 12/1997 | Lehan et al. | 356/445 |

Primary Examiner—Mark Hellner
Attorney, Agent, or Firm—Woodard, Emhardt, Naughton, Moriarty & McNett

[57] ABSTRACT

A method and apparatus for eliminating the effects of varying sample distance on optical measurements. In a first embodiment, a light source and a detector are both positioned in front of a measurement sample. A light source lens assembly focuses the light such that its focal point is behind the measurement sample, while a detector lens assembly focuses the light reflected from the measurement sample such that its focal point is in front of the measurement sample. Any movement of the measurement sample away from its nominal position does not affect the detector output because the effects of the source lens assembly and the detector lens assembly cancel each other. In a second embodiment, a light source and two detectors are positioned on one side off a measurement sample. The first detector is placed at a small angle relative to the sample normal, while the second detector is placed at a relatively large angle relative to the sample normal. A system output, which does not vary if the measurement sample is moved from its nominal position, comprises the weighted summation of the first and second detector outputs and a correction signal. The correction signal comprises a weighted difference of the first and second detector outputs.

20 Claims, 3 Drawing Sheets

5,801,817

METHOD AND APPARATUS FOR ELIMINATING THE EFFECTS OF VARYING SAMPLE DISTANCE ON OPTICAL MEASUREMENTS

TECHNICAL FIELD OF THE INVENTION

The present invention generally relates to a method and apparatus for analog optical measurements and, more particularly, to a method and apparatus for eliminating the effects of varying sample distance on optical measurements.

BACKGROUND OF THE INVENTION

Devices which measure reflectance or light intensity (such as luminescence) produced by a measurement sample are well known in the art. Such systems typically employ a source of light and a light intensity detector at a given distance and angle relative to the measurement sample. Because the measurement of such systems is based entirely upon the amount of light received from the measurement sample, any variability in the distance between the measurement sample and the light source and/or light detector will produce a variability in the reflectance measurement and, therefore, variability in the measurement results. Such systems therefore require precision repeatability in the positioning of the measurement sample with respect to the light source and light detector.

In order to overcome such sample distance variability, some prior art systems utilize a self-calibration process on the measurement sample itself. However, such mechanisms do not give reflectance values which are relative to a known standard. Such prior art methods also suffer from the inability to separate changes in blanking values from those changes in reflectance caused by aged or otherwise damaged measurement samples (i.e. test strips used in an optical blood glucose measurement device). An ability to distinguish such changes from changes due to positional variations is important from a reliability standpoint.

Complex methods for focus compensation of light source/detector systems have been utilized in prior art compact disc digital systems. The systems typically consist of specialized optical lensing and/or specialized photodetectors. Consequently, these systems are typically expensive and are subject to long term drift because of the complex nature of the system. These drawbacks preclude the use of such systems in less expensive devices, such as blood glucose monitoring meters.

There is therefore a need for a method of eliminating the effects of varying sample distance on optical measurements, and the present invention is directed toward meeting this need.

SUMMARY OF THE INVENTION

The present invention generally relates to a method and apparatus for eliminating the effects of varying sample distance on optical measurements. In a first embodiment, a light source and a detector are both positioned in front of a measurement sample. A light source lens assembly having a focal point behind the measurement sample focuses the light onto the measurement sample, while a detector lens assembly having a focal point in front of the measurement sample focuses the light reflected from the measurement sample onto the detector. Any movement of the measurement sample away from its nominal position does not affect the detector output because the effects of the source lens assembly and the detector lens assembly cancel each other. In a second embodiment, a light source and two detectors are positioned on one side of a measurement sample. The first detector is placed at a small angle relative to the sample normal, while the second detector is placed at a relatively large angle relative to the sample normal. A system output, which does not vary if the measurement sample is moved from its nominal position, comprises a weighted summation of the first and second detector outputs and a correction signal. The correction signal comprises a weighted difference of the first and second detector outputs.

In one form of the invention, a method for eliminating effects of varying sample distance on optical measurements is disclosed, comprising the steps of: a) placing a measurement sample at an actual position, wherein said actual position may differ from a desired, nominal position; b) providing a light source in front of the measurement sample; c) providing a source lens assembly between the light source and the measurement sample, wherein a source focal point of the source lens assembly lies on one side of the measurement sample; d) providing a light detector in front of the measurement sample; and e) providing a detector lens assembly between the detector and the measurement sample, wherein a detector focal point of the detector lens assembly lies on another side of the measurement sample.

In another form of the invention, an apparatus for eliminating effects of varying sample distance on optical measurements is disclosed, comprising a measurement sample placed at an actual position, wherein said actual position may differ from a desired, nominal position; a light source positioned in front of the measurement sample; a source lens assembly positioned between the light source and the measurement sample, wherein a source focal point of the source lens assembly lies on one side of the measurement sample; a light detector positioned in front of the measurement sample; and a detector lens assembly positioned between the detector and the measurement sample, wherein a detector focal point of the detector lens assembly lies on another side of the measurement sample.

In another form of the invention, a method for eliminating effects of varying sample distance on optical measurements is disclosed, comprising the steps of: a) placing a measurement sample at an actual position, wherein said actual position may differ from a desired, nominal position; b) providing a light source on one side of the measurement sample; c) providing a first light detector on the one side of the measurement sample, wherein the first light detector is placed at a first angle from a normal vector of the measurement sample; d) providing a second light detector on the one side of the measurement sample, wherein the second light detector is placed at a second angle from the normal vector of the measurement sample; e) creating a correction signal comprising a weighted difference between a first output of the first light detector and a second output of the second light detector; and f) creating a corrected output signal comprising a weighted summation of the first output, the second output and the correction signal.

In another form of the invention, an apparatus for eliminating effects of varying sample distance on optical measurements is disclosed, comprising a measurement sample placed at an actual position, wherein said actual position may differ from a desired, nominal position; a light source positioned on one side of the measurement sample; a first light detector on the one side of the measurement sample, wherein the first light detector is placed at a first angle from a normal vector of the measurement sample; a second light detector on the one side of the measurement sample, wherein the second light detector is placed at a second angle from the normal vector of the measurement sample; and an electrical circuit coupled to the first and second light detectors and operable to create a correction signal comprising a weighted difference between a first output of the first light detector and a second output of the second light detector; and a corrected output signal comprising a weighted summation of the first output, the second output and the correction signal.

DETAILED DESCRIPTION OF THE PREFERRED EMBODIMENTS

Figure 1:
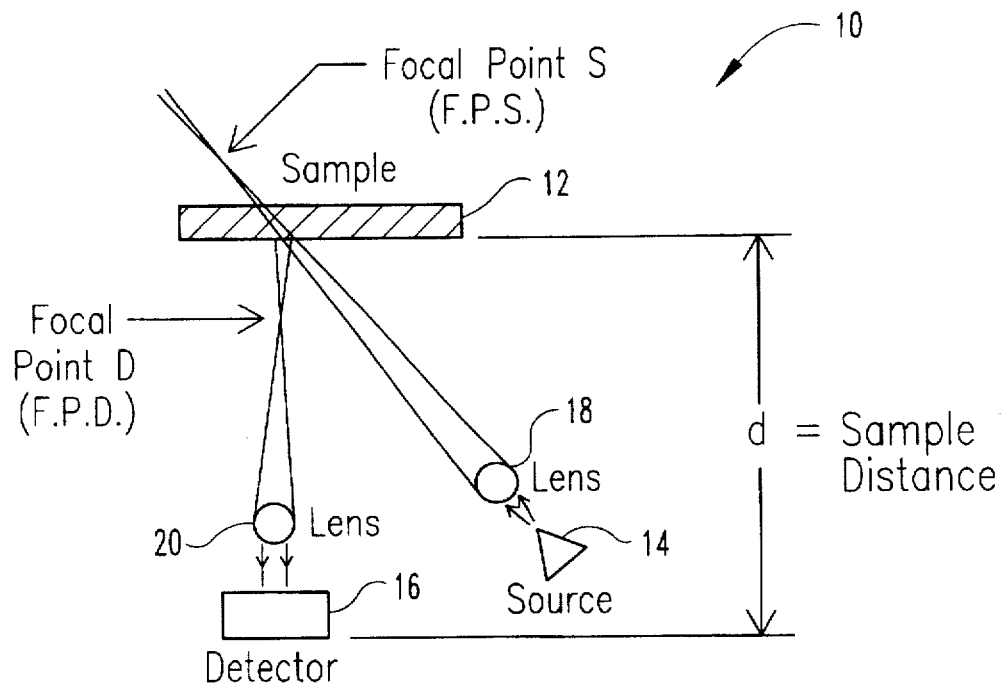
FIG. 1 is a schematic representation of a first embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention utilizes two distinct techniques for providing an optical reflectance measurement value which is independent of the distance between the light source and the measurement sample and the distance between the light detector and the measurement sample. A first embodiment of the present invention is illustrated schematically in FIG. 1, and indicated generally at 10. The system 10 includes a measurement sample 12, such as a test strip for use in a blood glucose measurement meter. A light source 14 is used to illuminate the measurement sample 12, and a photodetector 16 measures the amount of light reflected from the measurement sample 12. The quantity of light reflected by the measurement sample 12 (and therefore detected by the detector 16) provides valuable information about the measurement sample 12. Therefore, any change in the amount of light received by the detector 16 which is due to a variation in the sample distance d will impair the ability of the system 10 to provide information about the measurement sample 12.

The first embodiment of the present invention eliminates the effects of varying sample distance d by incorporating two lensing systems into the measurement system 10. The first such system is the lens assembly 18, which is operative to focus the light emanated by the light source 14 onto the measurement sample 12. The present invention comprehends the use of a single lens or a multiple lens assembly for the lens 18. The design of the lens 18 is such that the focal point S of the lens 18 lies behind the measurement sample 12 when the measurement sample 12 is in its nominal position. In other words, the focal length of the lens 18 is greater than the distance between the light source 14 and the measurement sample 12. This arrangement is illustrated in FIG. 1. Similarly, a second lens assembly 20, which may be a single lens or a multiple lens assembly, is positioned so as to focus light reflected by the measurement sample 12 onto the detector 16. The focal point D of the lens 20 is chosen such that it lies in front of the measurement sample 12 when the measurement sample 12 is at its nominal position. In other words, the focal length of the lens 20 is shorter than the sample distance d.

The measurement system 10 works by using the self-compensating effects of the lensing system 18, 20. If the measurement sample 12 moves closer to the source 14/detector 16 system, then the light intensity hitting the measurement sample 12 from the source 14 is smaller because the measurement sample 12 is now farther away from the focal plane of the source 14 (coinciding with the focal point S). However, because the detector 16 focal point D lies in front of the measurement sample 12, the light flux hitting the detector 16 is now larger. This is because the measurement sample 12 has moved closer to the focal plane of the lens 20 (coinciding with the focal point D). With the measurement system 10 of FIG. 1, the lensing effects of the source and the detector cancel each other out, thereby eliminating any measurement error associated with varying the sample distance d.

It will be appreciated by those skilled in the art that movement of the measurement sample 12 in the opposite direction (increasing sample distance d) results in the same cancelling effect. Furthermore, it will be appreciated by those skilled in the art that placing the focal point S in front of the measurement sample 12 and placing the focal point D behind the measurement sample 12 also produces the same effect.

Figure 2B:
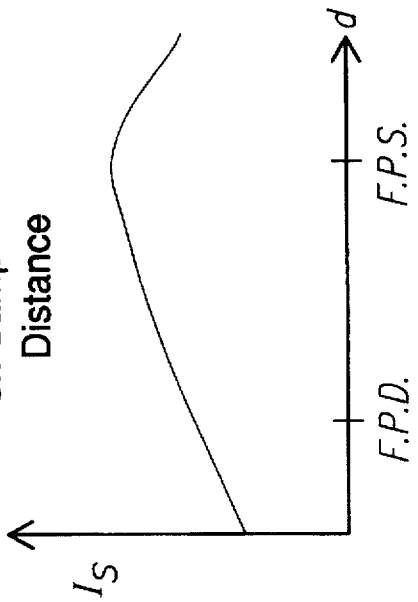
FIGS. 2A–C are graphs of light intensity v. sample distance for the first embodiment of the present invention.
Figure 2A:
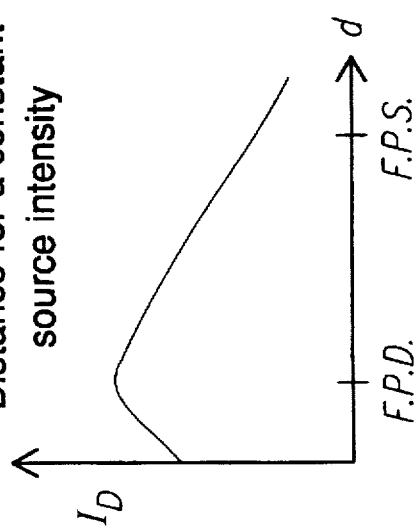
Figure 2C:
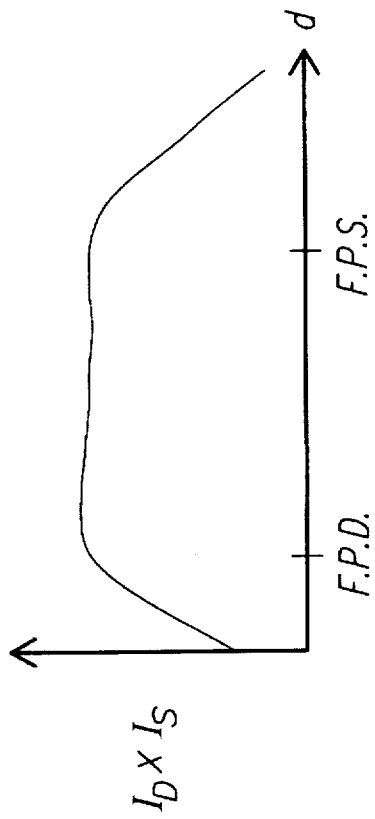

FIGS. 2A–C quantitatively illustrate the effects of the lenses 18 and 20 upon the system 10 of FIG. 1. In FIG. 2A, the intensity of light measured at the detector 16 is graphed versus sample distance d. The data of FIG. 2A assumes a constant source intensity (i.e. no lens 18). It can be readily seen that the detector response is at a maximum when the measurement sample 12 coincides with the plane of the focal point D, and that the detector response declines the further the measurement sample moves away from the focal point D in either direction. Similarly, FIG. 2B illustrates the intensity of light from the light source 14 which reaches the measurement sample 12 versus the sample distance d. The data of FIG. 2B assumes that the lens 18 is in place. It can be seen that the intensity of light impinging upon the measurement surface of the sample 12 is greatest when the sample distance d coincides with the plane of the focal point S. The intensity of light impinging upon the measurement sample 12 decreases as the measurement sample 12 moves away from the focal point S in either direction. FIG. 2C illustrates the combined effect of the lens 18 and the lens 20. Because the graphs of FIGS. 2A and 2B have maxima at different sample distances, combining the effects of these two graphs produces an essentially flat response for the system 10 when the sample distance d lies between the focal point S and the focal point D. It can therefore be seen that varying the sample distance between these two limits does not introduce any measurement error into the measurement system 10.

Figure 3:
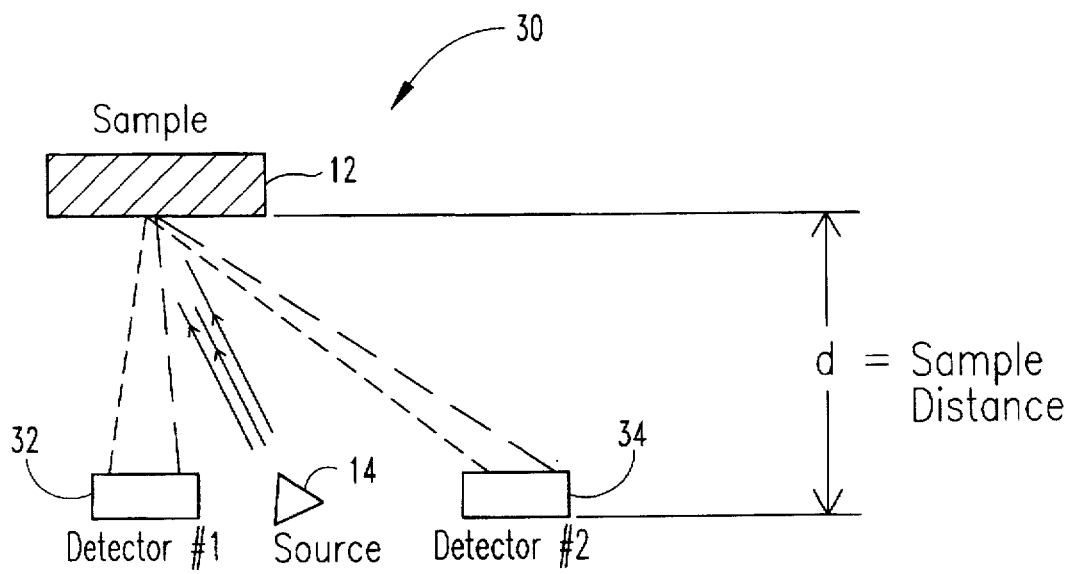
FIG. 3 is a schematic representation of a second embodiment of the present invention.

The second embodiment of the present invention comprises a reflectance measurement system having a single light source and a dual (or multiple) detector assembly consisting of multiple detectors placed at various angles with respect to the normal vector of the sample surface. A schematic diagram of a preferred form of the second embodiment of the present invention is illustrated in FIG. 3.

and indicated generally at 30. The measurement system 30 includes a measurement sample, for example a test strip in a blood glucose measurement system. A light source 14 illuminates a portion of the measurement sample 12 and light is reflected therefrom. A first detector 32 and a second detector 34 each receive a portion of the light reflected from the measurement sample 12, therefore the detector outputs vary with the amount of light reflected from the sample 12. As was the case with the first embodiment of the present invention, the outputs of the detectors 32 and 34 also vary with varying sample distance d. The present invention attempts to eliminate the effects of varying sample distance upon the response of the system 30.

The measurement system 30 makes use of the fact that detectors placed at different angles relative to the measurement sample 12 will respond to changes in the sample distance d differently. The specific response of the detector as a function of sample distance depends upon the emission characteristics of the sample being measured, the emission characteristics of the light source, and the detection characteristics of the detector. However, in general it can be said that the response of a detector at a large angle relative to the sample normal decreases more slowly (or can actually increase) relative to the response of a detector located at low angles relative to the sample normal. This effect can be used to compensate for varying sample distance d by electronically varying the gain of each detector amplifier and using the output from a difference amplifier in order to correct for the change in position. This can also be done digitally by converting the analog signals of the two detectors to digital values and using software algorithms to perform the required multiplications and subtractions.

Figure 4:
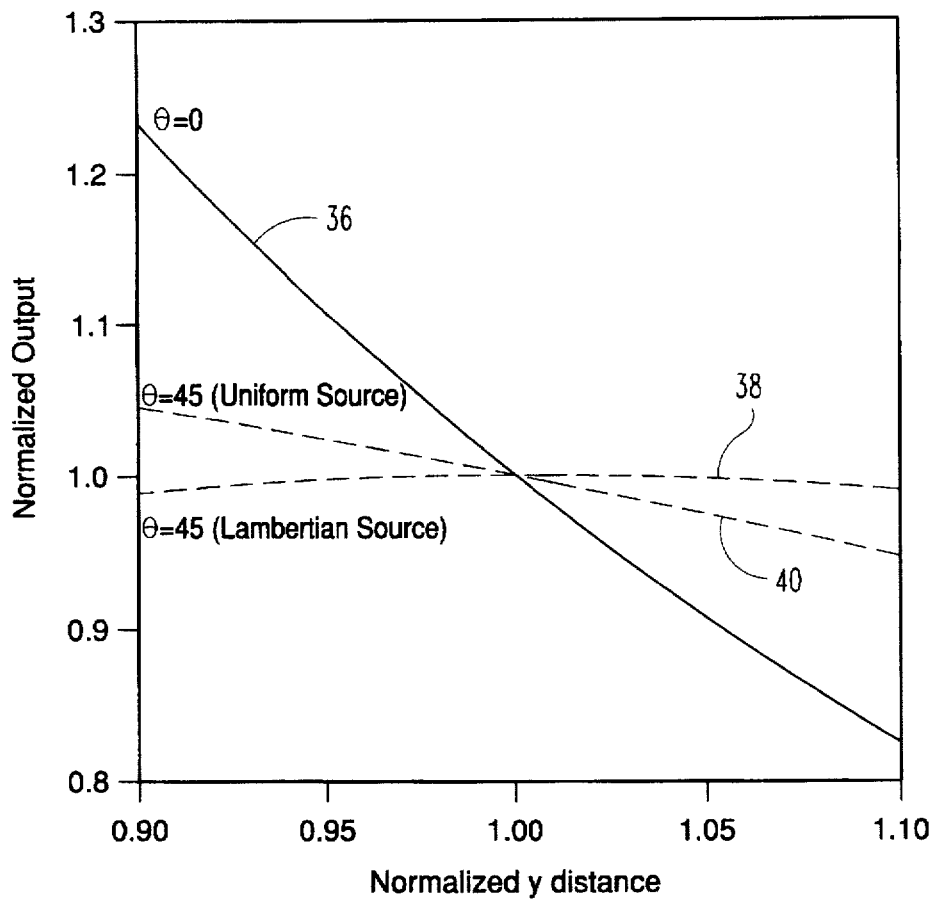
FIG. 4 is a graph of detector response v. sample distance for several detector angles in the second embodiment of the present invention.

FIG. 4 illustrates a graph of the normalized output for a photodetector versus the normalized sample distance. The response curve 36 corresponds to the output of detector 32 which is placed on the normal vector to the sample 12. It can be seen that the response of the detector 32 varies relatively greatly with varying sample distance d. On the other hand, the response of the detector 34, which is placed at a 456 angle relative to the sample normal, is shown in the curves 38 and 40. Two responses are shown in the graph of FIG. 4 because the response of the detector 34 is dependent upon the type of the measurement sample 12. Most samples are Lambertian, and will produce a response in detector 34 similar to that of line 38. Other samples, however, can show behavior closer to a uniform source and will produce a response from the detector 34 closer to that shown in line 40. In either case, it can be readily seen that the detector 34, which is placed at a relatively large angle from the sample normal, varies its output much less with varying sample distance d than does the detector 32 placed upon the sample normal.

Figure 5:
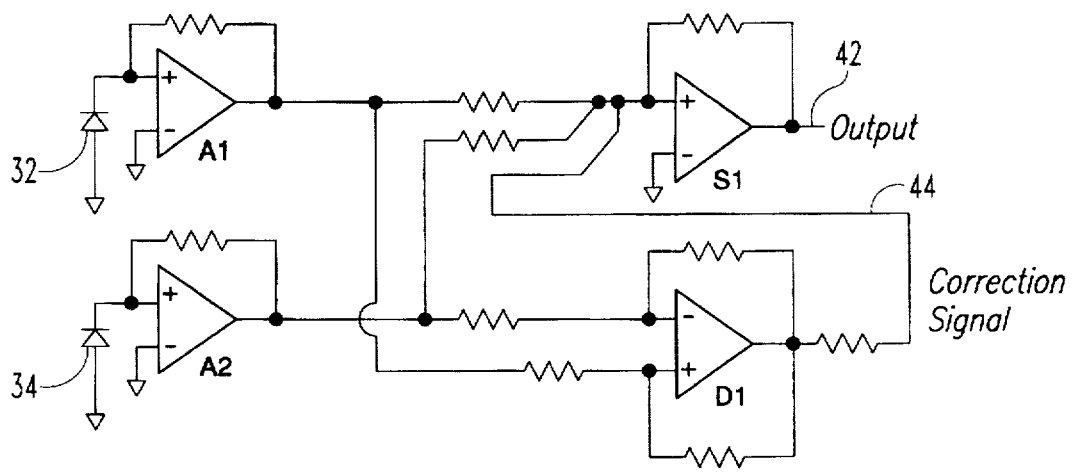
FIG. 5 is an electrical schematic diagram of a third embodiment electrical compensation circuit for use with the second embodiment of the present invention.

A schematic electrical diagram of a preferred embodiment circuit for processing the outputs of detectors 32 and 34 in order to produce an output for the measurement system 30 which eliminates the effects of varying sample distance d is shown in FIG. 5. The signal from the photodetector 32 is amplified by an amplifier A1 and the signal from the photodetector 34 is similarly amplified by an amplifier A2. The gains of the amplifiers A1 and A2 are chosen such that the output of each amplifier is equal at the nominal sample position. The output 42 of the measurement system 30 is produced by the summing amplifier S1 which adds the outputs from amplifiers A1 and A2. At the nominal sample distance, the output 42 of the measurement system 30 will equal twice the output of the individual detectors 32 and 34.

In order to correct for variations in the outputs of the detectors 32 and 34 when the measurement sample 12 is not in its nominal position, the outputs of amplifiers A1 and A2 are also input to the difference amplifier D1 in order to create the correction signal 44. The correction signal 44 comprises a signal which is equivalent to the weighted difference between the outputs of detectors 32 and 34. This correction signal 44 is also summed by the summing amplifier S1, such that any change in the response of detectors 32 and 34 caused by varying sample distance is eliminated by inclusion of the correction signal into the sum. In the instance of the detector responses graphed in FIG. 4, we can describe the amplifier outputs as approximately linear near the nominal position, specifically $$A_{1out} = I_0(m_1 x + b)$$

and $$A_{2out} = I_0(m_2 x + b)$$

where $I_o$ is the reflected light intensity, x is the distance from the nominal position, and $A_{1out}$ and $A_{2out}$ refer to the amplifier outputs corresponding to amplifiers A1 and A2 respectively. We see at nominal position, the outputs of both amplifiers are equal to $I_o b$. The sum of these signals for general positions is (without error correction)

$$A_{1out} + A_{2out} = I_0((m_1 + m_2)x + 2b)$$

This indicates that the output of the difference amplifier should be $$-I_o(m_1 + m_2)x$$

To achieve this value, a gain of $$-(m_1 + m_2)/(m_1 - m_2)$$

is required from the difference amplifier. When this output is added to the outputs $A_{1out}$ and $A_{2out}$ we obtain for the output 42 of the final amplifier S1

$$A_{final} = 2\lambda I_0 b$$

Where $\lambda$ refers to the gain of the final amplifier S1. To reduce correction errors, difference $(m_1 - m_2)$ should be large.

A comparison of the circuit of FIG. 5 with the detector responses graphed in FIG. 4 will illustrate that the circuit of FIG. 5 is effective in producing an output 42 which is dependent only upon the intensity of the light reflected by the measurement sample 12, and not (at least to the first order) upon the sample distance d. By addition of more detectors at different angles into the measurement system 30, one can also compensate for second order effects. In general, if there are n+1 detectors, an nth order correction can be made. It will be appreciated by those skilled in the art that the correction accomplished by the electronic circuit of FIG. 5 can also be accomplished via software by digitizing the signals at the detector outputs or at the outputs of the amplifiers A1 and A2.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the term "light source" as used herein is intended to encompass any source of electromagnetic energy, the term detector is intended to emcompass any means for detecting electromagnetic energy, and the term "lens assembly" is intended to encompass a single lens or multiple lens assembly and may include lenses of optical glass or any other device or method for altering the path of electromagnetic energy.

What is claimed is:

1. A method for eliminating effects of varying sample distance on optical measurements, comprising the steps of:
    a) placing a measurement sample at an actual position, wherein said actual position may differ from a desired, nominal position;
    b) providing a light source in front of the measurement sample;
    c) providing a source lens assembly between the light source and the measurement sample, wherein a source focal point of the source lens assembly lies on one side of the measurement sample;
    d) providing a light detector in front of the measurement sample; and
    e) providing a detector lens assembly between the detector and the measurement sample, wherein a detector focal point of the detector lens assembly lies on another side of the measurement sample.

2. The method of claim 1, wherein step (b) comprises providing a light source capable of emitting visible light.

3. The method of claim 1, wherein step (c) comprises providing a source lens assembly comprising a single lens.

4. The method of claim 3, wherein step (c) comprises providing a source lens assembly comprising a single lens constructed from optical glass.

5. The method of claim 1, wherein said one side of the measurement sample is in front of the measurement sample and said another side of the measurement sample is behind the measurement sample.

6. The method of claim 1, wherein step (d) comprises providing a photodetector diode in front of the measurement sample.

7. The method of claim 1, wherein step (e) comprises providing a detector lens assembly comprising a single lens.

8. The method of claim 7, wherein step (e) comprises providing a detector lens assembly comprising a single lens constructed from optical glass.

9. An apparatus for eliminating effects of varying sample distance on optical measurements, comprising:
    a measurement sample placed at an actual position, wherein said actual position may differ from a desired, nominal position;
    a light source positioned in front of the measurement sample;
    a source lens assembly positioned between the light source and the measurement sample, wherein a source focal point of the source lens assembly lies on one side of the measurement sample;
    a light detector positioned in front of the measurement sample; and
    a detector lens assembly positioned between the detector and the measurement sample, wherein a detector focal point of the detector lens assembly lies on another side of the measurement sample.

10. The apparatus of claim 9, wherein the light source is a visible light source.

11. The apparatus of claim 9, wherein the source lens assembly comprises a single lens.

12. The apparatus of claim 11, wherein the single lens is constructed of optical glass.

13. The apparatus of claim 9, wherein said one side of the measurement sample is in front of the measurement sample and said another side of the measurement sample is behind the measurement sample.

14. The apparatus of claim 9, wherein the light detector comprises a photodetector diode.

15. The apparatus of claim 9, wherein the detector lens assembly comprises a single lens.

16. The apparatus of claim 15, wherein the single lens is constructed of optical glass.

17. A method for eliminating effects of varying sample distance on optical measurements, comprising the steps of:
    a) placing a measurement sample at an actual position, wherein said actual position may differ from a desired, nominal position;
    b) providing a light source on one side of the measurement sample;
    c) providing a first light detector on the one side of the measurement sample, wherein the first light detector is placed at a first angle from a normal vector of the measurement sample;
    d) providing a second light detector on the one side of the measurement sample, wherein the second light detector is placed at a second angle from the normal vector of the measurement sample;
    e) creating a correction signal comprising a weighted difference between a first output of the first Light detector and a second output of the second light detector; and
    f) creating a corrected output signal comprising a weighted summation of the first output, the second output and the correction signal.

18. The method of claim 17, wherein the first angle is 0° and the second angle is 45°.

19. An apparatus for eliminating effects of varying sample distance on optical measurements, comprising:
    a measurement sample placed at an actual position, wherein said actual position may differ from a desired, nominal position;
    a light source positioned on one side of the measurement sample;
    a first light detector on the one side of the measurement sample, wherein the first light detector is placed at a first angle from a normal vector of the measurement sample;
    a second light detector on the one side of the measurement sample, wherein the second light detector is placed at a second angle from the normal vector of the measurement sample; and
    an electrical circuit coupled to the first and second light detectors and operable to create:
        a correction signal comprising a weighted difference between a first output of the first light detector and a second output of the second light detector; and
        a corrected output signal comprising a weighted summation of the first output, the second output and the correction signal.

20. The apparatus of claim 19, wherein the first angle is 0° and the second angle is 45°.

* * * * *

UNITED STATES PATENT AND TRADEMARK OFFICE
CERTIFICATE OF CORRECTION

PATENT NO : 5,801,817
DATED : September 1, 1998
INVENTOR(S) : Richard A. Riedel

It is certified that error appears in the above-identified patent and that said Letters Patent is hereby corrected as shown below:

In column 5, line 38, please change "456" to --45°--.

Signed and Sealed this

Seventh Day of September, 1999

*Attest:*

Q. TODD DICKINSON

*Attesting Officer*     *Acting Commissioner of Patents and Trademarks*